United States Patent
Zechlin et al.

(10) Patent No.: US 8,030,522 B2
(45) Date of Patent: Oct. 4, 2011

(54) PROCESS FOR THE PRODUCTION OF TOLUENE DIISOCYANATE

(75) Inventors: Joachim Zechlin, Neuss (DE); Bernd Pennemann, Bergisch-Gladbach (DE); Friedhelm Steffens, Leverkusen (DE); Wenbin Ji, League, TX (US)

(73) Assignees: Bayer MaterialScience LLC, Pittsburgh, PA (US); Bayer MaterialScience AG, Leverkusen (DE)

( * ) Notice: Subject to any disclaimer, the term of this patent is extended or adjusted under 35 U.S.C. 154(b) by 326 days.

(21) Appl. No.: 11/448,265

(22) Filed: Jun. 7, 2006

(65) Prior Publication Data

US 2007/0287857 A1    Dec. 13, 2007

(51) Int. Cl.
*C07C 39/02* (2006.01)

(52) U.S. Cl. .................................................. 564/416

(58) Field of Classification Search .................. None
See application file for complete search history.

(56) References Cited

U.S. PATENT DOCUMENTS

| 5,872,278 | A | 2/1999 | Kraus et al. ............... 560/347 |
| 6,140,539 | A | 10/2000 | Sander et al. ............. 564/421 |
| 6,900,348 | B1 | 5/2005 | Reif et al. ................. 560/347 |
| 2004/0092773 | A1* | 5/2004 | Forlin et al. ............... 564/416 |
| 2004/0118672 | A1 | 6/2004 | Grun et al. ................. 203/29 |

FOREIGN PATENT DOCUMENTS

| CA | 2209139 | 12/1997 |
| DE | 1 260 092 | 2/1968 |

* cited by examiner

*Primary Examiner* — Daniel Sullivan
*Assistant Examiner* — Yevegeny Valenrod
(74) *Attorney, Agent, or Firm* — N. Denise Brown; Noland J. Cheung

(57) ABSTRACT

The invention relates to a process for the production of toluene diisocyanate, in which the crude toluenediamine obtained from the hydrogenation is purified and then phosgenated. The purification step reduces the total amount of cyclic ketones to less than 0.1% by weight, based on 100% by weight of the toluenediamine.

6 Claims, No Drawings

PROCESS FOR THE PRODUCTION OF TOLUENE DIISOCYANATE

BACKGROUND OF THE INVENTION

The present invention relates to a process for the production of toluene diisocyanate, in which the crude toluenediamine obtained from the hydrogenation of dinitrotoluene is purified, and then phosgenated.

It is known that di- and poly-isocyanates are produced by phosgenation of the corresponding di- and poly-amines. In the case of distillable di- and poly-isocyanates, the phosgenation and separation of the solvent used are followed by distillation of the isocyanate. For example, toluene diisocyanate (TDI) is obtained in the form of a distilled product, whereas higher molecular weight mixtures of the polyisocyanates of the diphenylmethane series are obtained in undistilled form as bottom products.

In the working up of toluene diisocyanate (TDI), the crude product, which has largely been freed of solvent, is distilled to remove high-boiling constituents as well as low-boiling constituents that remain after the solvent has been separated off. Multi-stage distillations are thereby carried out in order to separate off low boilers and high boilers that remain in the crude product [see Industrielle Aromatenchemie, H.-G. Franck, J. Stadelhöfer, Springer-Verlag Berlin, 1987, p. 253], or alternatively, more energy-efficient integrated partition columns are used as described in U.S. Published Application 2004/118672, believed to correspond to EP-A1-1413571, or in DE-A1-1260092.

In the distillation of TDI, the markedly colored crude TDI product yields a water-clear, almost colorless end product. However, even finely distilled TDI is not completely free of color-imparting components, which occasionally leads to undesirable coloring of the TDI.

Undesirable coloring of distilled TDI product can have various causes, which require different processes for their avoidance.

For example, it is described in U.S. Pat. No. 6,900,348, believed to correspond to EP-A1-1 187 808, that the use of phosgene having a bromine content of <50 ppm in the production of isocyanates of the diphenyl-methane series can lead to a pale isocyanate on phosgenation.

Likewise, EP-A1-816 333 describes a process for reducing the color of TDI, in which the crude TDI solution is treated with hydrogen before the solvent is separated off.

In addition to treatment of the crude isocyanate product after phosgenation, treatment of the amine stream can also lead to a reduction in the color of the isocyanate produced by phosgenation. U.S. Pat. No. 5,872,278, which is believed to correspond to EP-A1-866 057, describes a process in which the amine is treated, prior to the reaction with phosgene, with solid substances containing Lewis-acidic and/or Brönstedt-acidic centres. The resulting isocyanate then has a lighter color than when the untreated amine is used.

SUMMARY OF THE INVENTION

It has now been found that the color value of distilled TDI can be markedly reduced if the toluenediamine (TDA) used in the phosgenation has a total content of cyclic ketones of less than 0.1% by weight, based on 100% by weight of the TDA used.

These cyclic ketones can come from the TDA and be based on a six-membered framework having zero, one or two double bonds. The double bonds may be conjugated with respect to the keto function, or alternatively, they may be isolated relative thereto. The cycloalkane framework or cycloalkene framework having zero, one or two double bonds may be substituted by one or two amino functions. It may also additionally be substituted by a methyl group.

Cyclic ketones in the TDA, or the precursors thereof, can form during the hydrogenation of dinitrotoluene (DNT), for example, by replacement of an amino function by water in an aqueous medium. The oxidative introduction of a keto function by oxidative attack during the nitration process is also possible, whereby nitrocresols can form.

In addition to the toluenediamine (TDA), commercial TDA conventionally also comprises by-products of the hydrogenation, such as, for example, TDA that has been completely or partially hydrogenated in the ring. If, for example, an amino function is replaced by water in TDA that has been completely or partially hydrogenated in the ring, then an aminomethylcyclohexanone or an aminomethylcyclohexenone is formed. If, for example, an amino function is replaced by water in TDA that has been completely or partially hydrogenated in the ring and that has additionally been deaminated, then a methylcyclohexanone or a methylcyclohexenone, for example, is formed. If, for example, both amino functions are replaced by water, methylcyclohexadiones can form. If nitrocresols from the production of dinitrotoluene pass into the hydrogenation, they can likewise be reacted therein to a cyclic ketone by partial hydrogenation in the ring.

In the subsequent phosgenation step, the cyclic ketones present in the TDA can then be phosgenated, and optionally, also chlorinated, whereby there can form in the first case, isocyanatocycloalkenones or isocyanatocycloalkanones, or in the second case, also chloroisocyanatocycloalkenes.

Because cyclic isocyanatocycloalkenones, isocyanatocycloalkanones and/or chloroisocyanatocycloalkenes are reactive substances, they are able to form adducts with TDI, with themselves or with other TDI by-products. Isocyanatocycloalkenones are able, for example, to enter into Diels-Alder reactions with dienes, or also with aromatic compounds (Angell, E. Charles; Fringuelli, Francesco; Guo, Ming; Minuti, Lucio; Taticchi, Aldo; Wenkert, Ernest. *Diels-Alder reactions of cycloalkenones. 14. Endo diastereoselectivity of 2-cyclohexenones in reactions with cyclopentadiene. Journal of Organic Chemistry* (1988), 53(18), 4325-8). Likewise, dimers can form (*An Enone-Dienol Tautomerism and an Iron (III)-Catalysed Dimerization of Cycloalkenone-2-carboxylates*. Christoffers, Jens. Institut für Organische Chemie, Technische Universität Berlin, Berlin, Germany. *Journal of Organic Chemistry* (1998), 63(13), 4539-4540). In the single- or multi-stage working up of crude TDI products by distillation, the cyclic isocyanatocycloalkenones, isocyanatocycloalkanones and/or chloroisocyanatocycloalkenes, as low boilers, can become concentrated in circulating streams in an undesirable manner, which further increases the reactivity for the formation of dimers or Diels-Alder adducts.

The dimers or Diels-Alder adducts formed from the isocyanatocycloalkenones, isocyanatocycloalkanones and/or chloroisocyanatocycloalkenes by reaction with TDI, with themselves or with other by-products, can be color-imparting to a greater or lesser degree. A significant proportion of these colored adducts or dimers formed during the distillation operation from cyclic isocyanatocycloalkenones, isocyanatocycloalkanones and/or chloroisocyanatocycloalkenes can then be discharged from the TDI distillation with the TDI stream, resulting in a colored TDI.

If a TDA stream having a total content of cyclic ketones of less than 0.1% by weight, based on 100% by weight of the TDA, is used in the phosgenation, the concentration of cyclic isocyanatocycloalkenones, isocyanatocycloalkanones and/or chloroisocyanatocycloalkenes in the TDI production, for example, in the circulating streams of the distillation of the TDI production process, can be so reduced that the formation of color-imparting adducts or dimers takes place to only a small degree. If fewer color-imparting adducts or dimers leave the process with the TDI product, then the TDI obtained as product is also markedly less colored.

DETAILED DESCRIPTION OF THE INVENTION

The invention relates to a process for the production of toluene diisocyanate by phosgenation of toluenediamine. This process comprises
a) hydrogenating dinitrotoluene in the presence of a catalyst, thus yielding a crude toluenediamine mixture,
b) purifying the crude toluenediamine mixture, thus yielding a toluenediamine which contains a total of less than 0.1% by weight of cyclic ketones, based on 100% by weight of the toluenediamine,
and
c) phosgenating the toluenediamine formed in b) which contains a total of less than 0.1% by weight of cyclic ketones, based on 100% by weight of the toluenediamine, thus yielding toluene diisocyanate.

In the toluenediamine obtained from the purifying step b), contains cyclic ketones in a total amount of less than 0.1% by weight, based on 100% by weight of the toluenediamine. The toluenediamine obtained in a) comprises the various TDA isomers, such as, 2,4-TDA, 2,6-TDA, 3,5-TDA (m-TDA), 2,5-TDA (p-TDA) and 2,3-TDA, 3,4-TDA (o-TDA), and the cyclic ketones, as well as various amounts of water, hexahydro-TDA, hexahydro-toluidine, nitrotoluidine, toluidine, and high boilers such as, for example, diphenylamine, diphenylmethane and/or phenazine derivatives. This toluenediamine typically comprises at least about 98% by weight of TDA.

The toluenediamine obtained the purification step b) comprises the cyclic ketones in a total amount of less than 0.1% by weight, preferably of less than 0.07% by weight, and more preferably of less than 0.04% by weight, based on 100% by weight of the toluenediamine. Preferably, the toluenediamine resulting from the purification step b) comprises alkylated cyclic ketones in concentrations of less than 0.1% by weight, and preferably of less than 0.07% by weight, based on 100% by weight of the toluenediamine.

The total amount (i.e. % by weight) of the cyclic ketones present is to be understood as meaning the total weight of all cyclic ketones which remain in the purified toluenediamine after step b). These cyclic ketones include, for example, methyl-substituted, ethyl-substituted or unsubstituted cycloalkanones, cycloalkenones, aminocycloalkanones, aminocycloalkenones and cycloalkadiones, preferably methylcyclohexanones, methylcyclohexenones, aminomethylcyclohexanones, aminomethylcyclohexenones and methylcyclohexadiones, and more preferably aminomethylcyclohexanones and aminomethylcyclohexenones.

In accordance with the present invention, the hydrogenation of dinitrotoluene in the presence of a catalyst in step a) is carried out, in a conventional manner, in reaction vessels which contain the catalyst such as, for example, nickel catalysts or noble metal catalysts, in the form of a suspension, a fluidised bed or a fixed bed. Such processes are known from the prior art and are described in, for example DE 2135154, DE 3734344, U.S. Pat. No. 5,563,296 which is believed to correspond to EP-634391 A, U.S. Pat. No. 5,779,995 which is believed to correspond to DE 4435839 A, U.S. Published Applications 2003/049185, 2003/050510 and 2005/129594 which are believed to correspond to EP-1287884 A, U.S. Pat. No. 6,005,143 which is believed to correspond to EP-978505 A, and U.S. Pat. No. 6,140,539 which is believed to correspond to EP-1033361 A, the disclosures of which are hereby incorporated by reference. The hydrogenation reaction can be carried out in the gas phase, or alternatively, in the liquid phase. The mixing power necessary in the case of reaction in the liquid phase can be introduced via a stirrer or via a nozzle into an internal and/or external circulating pump. Dissipation of heat can be carried out by a heat exchanger in the reactor, or alternatively, in the external circuit. If the catalyst is a fixed-bed catalyst, it can be present in the form of a trickling bed or in the form of a monolith. In the case of hydrogenation in the liquid phase, the hydrogenation can be carried out with or without the use of an additional solvent. In the case of hydrogenation in the gas phase, the hydrogenation can be carried out with or without the use of a carrier gas.

Following the hydrogenation, the crude TDA mixture is purified in step b). Purification can be carried out by distillation, crystallisation and/or thermal after-treatment, as well as by chemical oxidation or reduction processes.

In a preferred embodiment of the process, the purification process in step b) is carried out by distillation, and accordingly, water of reaction as well as low-boiling by-products, such as hexahydro-toluidine, hexahydro-TDA, and optionally, solvent, are removed partially or completely. This separation of water, low boilers, and optionally solvent, can be carried out in one or more steps. It is preferably followed by the removal of one or more of the o-TDA isomers by distillation, with it being possible for this separation of o-TDA by distillation to be carried out in one or more steps. Following this, high boilers are preferably separated by distillation from the m-TDA that remains.

According to the prior art, the separation of high boilers from the m-TDA is conventionally carried out by the use of simple combinations of evaporators and condensers, as are described in, for example, U.S. Pat. No. 6,359,177, the disclosure of which is herein incorporated by reference. It has been found, however, that this process does not necessarily yield a TDA having a total content of cyclic ketones <0.1% by weight.

Therefore, in a preferred embodiment of the process according to the invention, water of reaction, low boilers and, optionally, solvent as well as o-TDA are first removed partially or completely from the crude toluenediamine mixture, and high boilers and cyclic ketones are then separated either partially or completely from the m-TDA. The separation of high boilers and cyclic ketones from the m-TDA is preferably carried out with the aid of a distillation column having an evaporator and a condenser. The separation is preferably carried out at an absolute head pressure of from 50 to 2000 mbar, more preferably from 60 to 500 mbar and most preferably from 70 to 200 mbar. Head temperatures of preferably from 140 to 320° C., more preferably from 190 to 260° C. and most preferably from 195 to 230° C. are thereby obtained. The column has preferably at least 3, more preferably at least 5 and most preferably from 7 to 20 theoretical plates in the stripping section. There may also be used as separation aid any inserted elements known to the person skilled in the art, such as sieve, bubble-cap or valve plates or ordered or unordered packing materials. The pressure loss through the separation aid should be kept low, and is preferably less than 150 mbar, and more preferably less than 100 mbar. Bulk packing materials and ordered packing materials preferably have a specific surface area of from 100 to 500 $m^2/m^3$, and more preferably from 200 to 350 $m^2/m^3$. The bottom temperature is determined by the contents of high boilers and the pressure loss in the column; with the operating conditions of the column preferably being chosen such that bottom temperatures of <260° C., and more preferably <240° C. are obtained. The number of theoretical plates in the rectifying section and the reflux ratio are governed by the required content of cyclic ketones in the product. It has been found, however, that the process according to the invention can also be carried out without a rectifying section. This is advantageous in terms of the costs of the process.

In an alternate preferred embodiment of the process according to the invention, the water of reaction, low boilers and optionally solvent are first removed partially or completely from the crude toluenediamine, and then o-TDA, high boilers and cyclic ketones are separated partially or completely from the m-TDA. The separation of o-TDA, high boilers and cyclic ketones by distillation can be carried out in a single- or multi-stage distillation sequence using a partition column, which advantageously combines the separation of o-TDA and high boilers. As the feed to the partition column, it is preferred to use a crude toluenediamine mixture which has been freed partially or completely of water of reaction, low boilers and optionally solvent, and which comprises less than 0.5% by weight of cyclic ketones, and more preferably less than 0.3% by weight of cyclic ketones, based on 100% by weight of the toluenediamine.

Partition columns suitable herein have already been described several times as in, for example, U.S. Published Application 2003/0230476 A1, the disclosure of which is hereby incorporated by reference. In this preferred variation of the process according to the present invention, the m-TDA depleted of cyclic ketones is preferably removed as a side stream. The side stream is preferably removed at the level of the partition, that is to say, laterally from the partition. The cyclic ketones are thereby discharged partially or completely from the bottom of the partition column with the high boilers. Preferably, the separation is carried out at an absolute head pressure of from 50 to 2000 mbar, more preferably from 60 to 500 mbar and most preferably from 70 to 200 mbar. In the stripping section, beneath the side stream removal of the m-TDA, the column has preferably at least 5, more preferably at least 6 and most preferably from 7 to 20 theoretical plates. There may also be used as separation aid any inserted elements which are known to the person skilled in the art, such as sieve, bubble-cap or valve plates or ordered or unordered packing materials. The pressure loss through the separation aid should be kept low, and is preferably less than 150 mbar and more preferably less than 100 mbar. Bulk packing materials and ordered packing materials preferably have a specific surface area of from 100 to 500 $m^2/m^3$, and more preferably from 200 to 350 $m^2/m^3$. The bottom temperature is determined by the contents of high boilers and the pressure loss in the column; with the operating conditions of the column preferably being chosen such that bottom temperatures of <260° C., and more preferably <240° C. are obtained.

During the purification in step b), a significant reduction in the total content of cyclic ketones present in the TDA is preferably achieved. The total content by weight of cyclic ketones present in the TDA is preferably reduced in step b) by more than 25% by weight, and more preferably by more than 40% by weight.

After the purification in step b), a purified toluenediamine is obtained. This purified toluenediamine comprises less than 0.1% by weight of cyclic ketones in total, based on 100% by weight of the toluenediamine.

A relatively low content of cyclic ketones in the TDA crude mixture can already be established by suitably choosing the conditions for the hydrogenation in step a). According to the prior art, different catalysts, different reactors and different temperatures and pressures can be used in the production of TDA. Examples of these variations which are known in the prior art that may be mentioned here include, for example DE 2135154, DE 3734344, U.S. Pat. No. 5,563,296 which is believed to correspond to EP-634391 A, U.S. Pat. No. 5,779,995 which is believed to correspond to DE 4435839 A, U.S. Published Applications 2003/049185, 2003/050510 and 2005/129594 which are believed to correspond to EP-1287884 A, U.S. Pat. No. 6,005,143 which is believed to correspond to EP-978505 A, and U.S. Pat. No. 6,140,539 which is believed to correspond to EP-1033361 A, the disclosures of which are hereby incorporated by reference. However, the processes described in these references for the hydrogenation of dinitrotoluene to TDA do not result in a crude TDA mixture having a total content of cyclic ketones of <0.1% by weight.

By optimising the hydrogenation conditions (e.g. hydrogenation catalyst used, fundamental reaction parameters such as pressure, temperature, dwell time), the content of cyclic ketones in the crude TDA mixture produced by the hydrogenation process can, however, be reduced. For example, it is possible to produce a crude TDA mixture having a relatively low content of cyclic ketones by choosing a combination of a highly selective catalyst, a low temperature and a short dwell time of the TDA product in the reaction system. Suitable catalysts are, for example, highly selective doped or undoped Raney nickel catalysts, doped or undoped nickel catalysts fixed to a support, or noble metal catalysts fixed to a support and loaded with one or more noble metals. Suitable hydrogenation conditions are, for example, 120 to 180° C., 20 to 40 bar hydrogen pressure, and 0.5 to 4 hours dwell time in the reaction system.

In addition, the content of cyclic ketones in the crude TDA mixture that is produced in step a) can be further reduced by using, for the hydrogenation step, a dinitrotoluene that has a low content of nitrocresols such as, for example, <0.05% by weight.

The purified toluenediamine from step b) which contains a total amount of less than 0.1% by weight of cyclic ketones, based on 100% by weight of the toluenediamine, is then phosgenated in step c). The phosgenation can be carried out in the liquid phase. Suitable solvents are preferably unsubstituted and suitably substituted aromatic or aliphatic solvents having from 5 to 12 carbon atoms, such as toluene, chlorobenzene, benzene, dichlorobenzene, trichlorobenzene, decalin, tetralin, cyclohexane, hexane, cycloheptane, heptane, octane, nonane, decane, xylene, or mixtures of these solvents.

Particular preference of solvents is given to the use of benzene, toluene, chlorobenzene, dichlorobenzene.

The phosgenation of the toluenediamine can also be carried out in the gas phase, the toluenediamine being used above or below the boiling point at the appropriate pressure.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

Examples 1 to 3

5.4 t/h of toluenediamine (TDA) containing the amount of cyclic ketones as set forth in Table 1 were phosgenated in an industrial TDI production process. The phosgenation was carried out in perforated-base columns at a temperature of from 70 to 125° C. The pure TDI was obtained by separating off the solvent and distilling the crude TDI stepwise at temperatures of from 140 to 160° C. The last distillation step was carried out in a packed partition column, in which high boilers were concentrated and separated off at the bottom and a large part of the low boilers contained in the inlet stream were concentrated and separated off at the head. The high boilers were discharged from the process by subsequent concentration by evaporation; the low boilers were fed back into the solvent circuit.

The color of the pure TDI so obtained was analysed using a LICO 200 measuring device. The measured color index for each of Examples 1-3 are also set forth in Table 1.

The TDA used in Examples 1 to 3 was obtained by blending two TDA fractions:

Fraction A: was produced by hydrogenating dinitrotoluene in a stirred vessel at a pressure of 25 bar. The catalyst used was a nickel catalyst. In the sequence of separation by distillation downstream of the TDA reaction, water, low boilers and o-TDA were removed from the crude product.

Fraction B: was produced by hydrogenating dinitrotoluene in a stirred vessel at from 120 to 140° C. at a pressure of from 15 to 30 bar. The catalyst used was a nickel catalyst. In the sequence of separation by distillation downstream of the TDA reaction, water, low boilers, o-TDA, high-boiling residue and a portion of the cyclic ketones present were removed from the crude product.

TABLE 1

| | Sum of cyclic ketones in the TDA [% by weight] | Color index [APHA] | relative amount fraction A/ fraction B |
|---|---|---|---|
| Example 1 | 0.04 | 15 | 0:100 |
| Example 2 | 0.09 | 22 | 50:50 |
| Example 3 | 0.15 | 48 | 100:0 |

Examples 4 to 5

10.5 t/h of toluenediamine (TDA) containing the amount of cyclic ketones as set forth in Table 2 below were phosgenated in an industrial TDI production process. The phosgenation was carried out in perforated-base columns at a temperature of from 70 to 125° C. The pure TDI was obtained by separating off the solvent and distilling the crude TDI stepwise at temperatures of from 140 to 180° C. The last distillation step was carried out in a packed column, in which high boilers were concentrated and separated off at the bottom, and some of the low boilers contained in the inlet stream were concentrated and separated off at the head. The high boilers were discharged from the process by subsequent concentration by evaporation; and the low boilers separated off at the head were fed back into the solvent circuit.

The color of the pure TDI so obtained was analysed using a LICO 200 measuring device. The color index measured is shown in the table.

The TDA used in Example 4 and Example 5 was produced by hydrogenating dinitrotoluene in a stirred vessel at a pressure of 25 bar. The catalyst used was a nickel catalyst. In the sequence of separation by distillation downstream of the TDA reaction in Example 5, water, low boilers, o-TDA, the high-boiling residue, and also, more than 25% of the cyclic ketones present were removed from the crude product.

In the case of the TDA used in Example 4, a further 65% of the cyclic ketones present were additionally separated off by distillation by improving the separating efficiency of the last distillation step as compared with Example 5.

TABLE 2

| | Sum of cyclic ketones in the TDA [% by weight] | Color index [APHA] |
|---|---|---|
| Example 4 | 0.03 | 12 |
| Example 5 | 0.09 | 20 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of toluene diisocyanate comprising:
    a) hydrogenating dinitrotoluene at temperatures of from 120 to 180° C. under 20 to 40 bar hydrogen pressure and at 0.5 to 4 hours dwell time, in the presence of a catalyst which is selected from the group consisting of doped or undoped Raney nickel catalysts, doped or undoped nickel catalysts fixed to a support and noble metal catalysts fixed to a support and loaded with one or more noble metals, to yield a crude toluenediamine mixture,
    b) purifying the crude toluenediamine mixture in a multistage distillation, which comprises a stage in which the high boilers and cyclic ketones are separated off with the aid of a distillation column comprising an evaporator, a condenser and a stripping section, said stripping section having at least 3 theoretical plates, wherein said distillation column is operated at absolute head pressures of from 50 to 2000 mbar and at head temperatures of from 140 to 320° C., to yield a toluenediamine which contains a total of less than 0.1% by weight of cyclic ketones, based on 100% by weight of the toluenediamine, and
    c) phosgenating the toluenediamine which contains a total of less than 0.1% by weight of cyclic ketones, based on 100% by weight of the toluenediamine, to yield the toluene diisocyanate.

2. The process of claim 1, in which the toluenediamine obtained in step b) contains a total concentration of less than 0.1% by weight of alkylated cyclic ketones, based on 100% by weight of the toluenediamine.

3. The process of claim 1, in which the cyclic ketones are methyl-substituted, ethyl-substituted or unsubstituted cycloalkanones, cycloalkenones, aminocycloalkanones, aminocycloalkenones and/or cycloalkadiones.

4. The process of claim 1, in which the total amount by weight of cyclic ketones present in the toluenediamine mixture formed in step a) is reduced by more than 25% in step b).

5. The process of claim 1, in which the crude toluenediamine mixture formed in step a) contains less than 0.5% by weight of cyclic ketones.

6. The process of claim 1, in which the crude toluenediamine mixture formed in step a) contains less than 0.3% by weight of cyclic ketones.

* * * * *